(12) United States Patent  
Hölzl et al.

(10) Patent No.: US 6,814,960 B1  
(45) Date of Patent: Nov. 9, 2004

(54) HYDROXYSTILBENE COMPOUNDS USED AS MICROBICIDAL ACTIVE SUBSTANCES

(75) Inventors: Werner Hölzl, Eschentzwiller (FR); Dietmar Ochs, Schopfheim (DE); Wolfgang Haap, Grenzach-Wyhlen (DE); Karin Puchtler, Fischingen (DE); Marc I Schnyder, Birsfelden (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/806,844

(22) PCT Filed: Oct. 2, 1999

(86) PCT No.: PCT/EP99/07313

§ 371 (c)(1),
(2), (4) Date: Apr. 5, 2001

(87) PCT Pub. No.: WO00/21368

PCT Pub. Date: Apr. 20, 2000

(30) Foreign Application Priority Data

Oct. 9, 1998 (EP) ............................................. 98811006

(51) Int. Cl.$^7$ .............................. A61K 7/32; A61K 7/06
(52) U.S. Cl. ......................... 424/65; 424/70.1; 514/733; 568/744
(58) Field of Search ................................ 422/28, 40, 5; 514/733; 8/115.51; 510/461; 568/744; 424/65, 70.1

(56) References Cited

U.S. PATENT DOCUMENTS

| 3,577,230 A | | 5/1971 | Sheers ........................... 71/67 |
| 3,678,168 A | * | 7/1972 | Grier .................... 106/18.31 X |
| 6,197,834 B1 | * | 3/2001 | Docherty ..................... 514/733 |

FOREIGN PATENT DOCUMENTS

| FR | 2020995 | 7/1970 |
| WO | 95/03695 | 2/1995 |

OTHER PUBLICATIONS

Athanassopoulos, P. et al. Abstract of "Application of resins of the trityl type in solid phase organic synthesis, "1997, Pharmakon–Press, Epitheorese Klinikes Farmakologias kia farmakokinetikes, International Edition, 11(2 and 3), pp. 122–124.*

Chem. Abstr. vol. 128, No. 13, (1998), No. 158748 for JP 10045566.

Chem. Abstr. vol. 128, No. 7, (1998), No. 79811 for JP 09328410.

Chem. Abstr. vol. 108, No. 3, (1988), No. 17670 for Acta. Amazonica, vol. 15, No. 3–5, (1985), pp. 321–325.

\* cited by examiner

Primary Examiner—Elizabeth McKane  
(74) Attorney, Agent, or Firm—Kevin T. Mansfield

(57) ABSTRACT

The use of hydroxystilbene compounds of formula

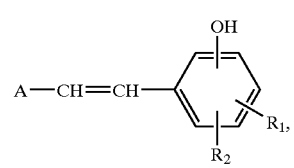

(1)

wherein  
A is a radical of formula

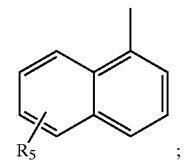

(1a)

or a radical of formula

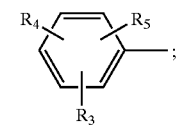

(1b)

and  
$R_1, R_2, R_3, R_4$ and $R_5$ are each independently of the others hydrogen, halogen, hydroxy, $C_1-C_{16}$alkyl, $C_1-C_{16}$alkoxy, phenyl; $C_1-C_3$phenylalkyl; $C_6-C_{10}$aryloxy, amino, mono-$C_1-C_5$alkylamino, di-$C_1-C_5$alkylamino, or —$NO_2$;  
as microbicidal active ingredients is described.

The compounds exhibit a pronounced action against pathogenic gram-positive and gram-negative bacteria, and also against yeasts and moulds. They are therefore suitable for the antimicrobial treatment, especially the preservation and disinfection, of surfaces.

4 Claims, No Drawings

HYDROXYSTILBENE COMPOUNDS USED AS MICROBICIDAL ACTIVE SUBSTANCES

The present invention relates to the use of hydroxystilbene compounds in the antimicrobial treatment of surfaces.

The hydroxystilbene compounds used according to the invention correspond to formula

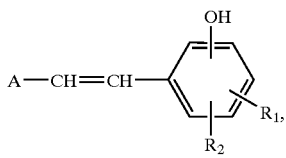
(1)

wherein

A is a radical of formula

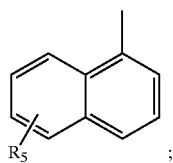
(1a)

or a radical of formula

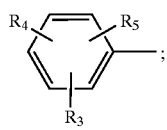
(1b)

and $R_1, R_2, R_3, R_4$ and $R_5$ are each independently of the others hydrogen, halogen, hydroxy, $C_1$–$C_{16}$alkyl, $C_1$–$C_{16}$alkoxy, phenyl; $C_1$–$C_3$phenylalkyl; $C_6$–$C_{10}$aryloxy, amino, mono-$C_1$–$C_5$alkylamino, di-$C_1$–$C_5$alkylamino, or —$NO_2$.

$C_1$–$C_{16}$Alkyl are straight-chain or branched alkyl radicals, e.g. methyl, ethyl, n-propyl, isopropyl, n-butyl, sec-butyl, tert-butyl, amyl, isoamyl or tert-amyl, heptyl, octyl, isooctyl, nonyl, decyl, undecyl, dodecyl, tetradecyl, pentadecyl or hexadecyl.

$C_1$–$C_{16}$Alkoxy is e.g. methoxy, ethoxy, n-propoxy, isopropoxy, n-butoxy, sec-butoxy, tert-butoxy, amyloxy, isoamyloxy or tert-amyloxy, hexyloxy, heptyloxy, octyloxy, isooctyloxy, nonyloxy, decyloxy, undecyloxy, dodecyloxy, tetradecyloxy, pentadecyloxy or hexadecyloxy.

$C_6$–$C_{10}$Aryloxy is phenoxy or naphthyloxy.

Halogen is fluorine, chlorine, bromine or iodine.

The hydroxystilbenes used according to the invention can be in the form of E- or Z-isomers.

They are preferably in the form of E-isomers.

Interesting compounds that are used according to the invention are dihydroxystilbenes, that is to say compounds of formula (1) wherein $R_1$ and $R_2$ are hydroxy.

Very special preference is given to the use of compounds of formula

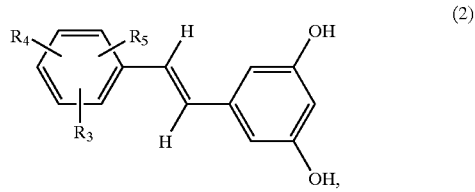
(2)

wherein $R_3$, $R_4$ and $R_5$ are as defined for formula (1), and more especially those compounds of formula (2) wherein $R_3$, $R_4$ and $R_5$ are hydrogen.

Also preferred are compounds of formula

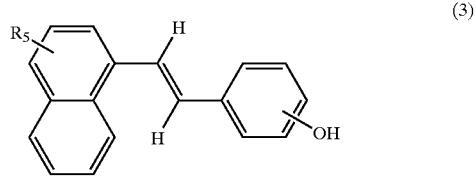
(3)

wherein $R_5$ is as defined for formula (1) and is especially hydrogen.

The compounds of formula (3) are novel and the invention relates also thereto.

The preparation of the compounds of formula (1) is carried out in accordance with processes known per se by reaction of an alkyl phosphite, e.g. triethyl phosphite, with a benzyl halide, preferably benzyl bromide. The phosphonate intermediate is obtained (1st step).

The phosphonate intermediate is then reacted with an alkoxybenzaldehyde (2nd step). The subsequent dealkylation (3rd step) is carried out in accordance with customary methods.

The entire reaction sequence can be illustrated as follows:

1st Step

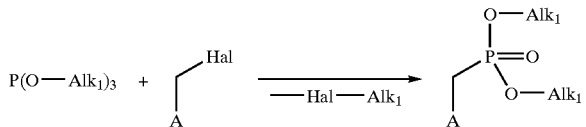

2nd Step

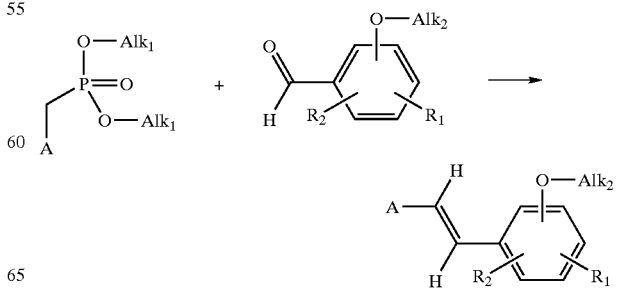

3rd Step

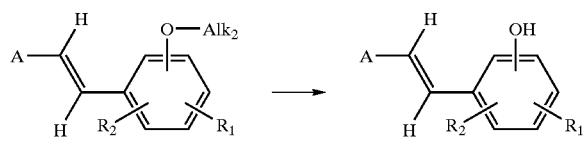

More details relating to this reaction can be found in Can. J. Chem. 48, 1554 (1970).

In a further variant, the hydroxystilbene compounds according to the invention can be prepared in a solid-phase synthesis using a trityl resin. The preparation is carried out in accordance with the following scheme:

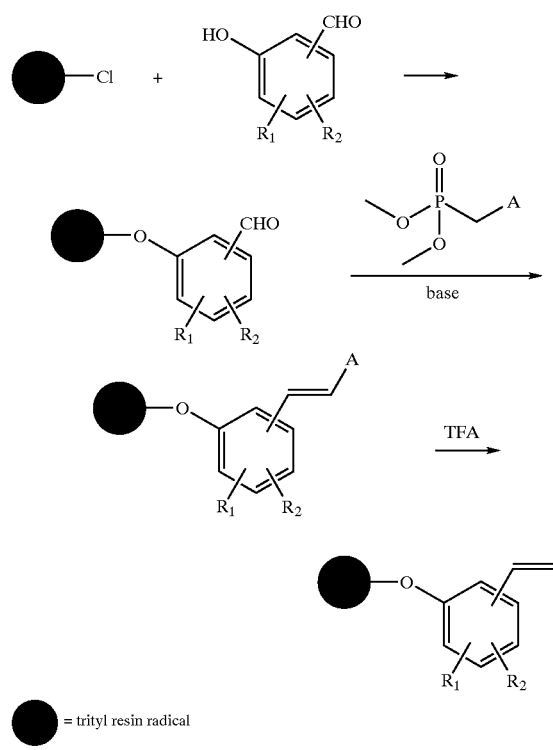

● = trityl resin radical wherein $R_1$, $R_2$ and A are as defined for formula (1).

The method of synthesis is based on the literature procedure of R. Willard et al., Chemistry & Biology, 2, 1995, 45–51. The distinguishing feature of the preparation process according to the invention lies in the use of the trityl resin and the different method used for loading the resin.

More details relating to the preparation process according to the invention can be found in the corresponding Examples.

The hydroxystilbene compounds used according to the invention exhibit a pronounced antimicrobial action, especially against pathogenic gram-positive and gram-negative bacteria and also against bacteria of skin flora, e.g. Corynebacterium xerosis (bacteria that cause body odour), and also against yeasts and moulds. They are therefore especially suitable in the disinfection of the skin and mucosa and also of integumentary appendages (hair), more especially in the disinfection of the hands and of wounds.

They are therefore suitable as antimicrobial active ingredients and preservatives in personal care preparations, for example shampoos, bath additives, hair-care products, liquid and solid soaps (based on synthetic surfactants and salts of saturated and/or unsaturated fatty acids), lotions and creams, deodorants, other aqueous or alcoholic solutions, e.g. cleansing solutions for the skin, moist cleansing cloths, oils or powders.

The invention therefore relates also to a personal care preparation comprising at least one compound of formula (1) as well as cosmetically tolerable carriers or adjuvants.

The personal care preparation according to the invention comprises from 0.01 to 15% by weight, preferably from 0.1 to 10% by weight, based on the total weight of the composition, of the hydroxystilbene compound of formula (1), and cosmetically tolerable adjuvants.

Depending upon the form of the personal care preparation, it will comprise, in addition to the stilbene compound of formula (1), further constituents, for example sequestering agents, colourings, perfume oils, thickening or solidifying agents (consistency regulators), emollients, UV absorbers, skin-protective agents, antioxidants, additives that improve mechanical properties, such as dicarboxylic acids and/or Al, Zn, Ca and Mg salts of $C_{14}$–$C_{22}$ fatty acids, and optionally preservatives.

The personal care preparation according to the invention may be formulated as a water-in-oil or oil-in-water emulsion, as an alcoholic or alcohol-containing formulation, as a vesicular dispersion of an ionic or non-ionic amphiphilic lipid, as a gel, a solid stick or as an aerosol formulation.

As a water-in-oil or oil-in-water emulsion, the cosmetically tolerable adjuvant contains preferably from 5 to 50% of an oily phase, from 5 to 20% of an emulsifier and from 30 to 90% water. The oily phase may contain any oil suitable for cosmetic formulations, e.g. one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Cosmetic formulations according to the invention may be contained in a variety of cosmetic preparations. Especially the following preparations, for example, come into consideration:

skin-care preparations, e.g. skin-washing and cleansing preparations in the form of tablet-form or liquid soaps, soapless detergents or washing pastes;

bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

intimate hygiene preparations, e.g. intimate washing lotions or intimate sprays;

foot-care preparations, e.g. foot baths, foot powders, foot creams or foot balsams, special deodorants and anti-perspirants or callus-removing preparations;

light-protective preparations, such as sun milks, lotions, creams and oils, sun blocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. soapless detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or after-shave lotions;

fragrance preparations, e.g. fragrances (eau de Cologne, eau de toilette, eau de parfum, parfum de toilette, perfume), perfume oils or cream perfumes;

dental-care, denture-care and mouth-care preparations, e.g. toothpastes, gel tooth-pastes, tooth powders, mouthwash concentrates, anti-plaque mouthwashes, denture cleaners or denture fixatives;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

An antimicrobial soap has, for example, the following composition:

0.01 to 5% by weight of the compound of formula (1)

0.3 to 1% by weight titanium dioxide 1 to 10% by weight stearic acid ad 100% soap base, e.g. the sodium salts of tallow fatty acid and coconut fatty acid or glycerol.

A shampoo has, for example, the following composition:

0.01 to 5% by weight of the compound of formula (1)

12.0% by weight sodium laureth-2-sulfate 4.0% by weight cocamidopropyl betaine 3.0% by weight NaCl and water ad 100%.

A deodorant has, for example, the following composition:

0.01 to 5% by weight of the compound of formula (1)

60% by weight ethanol 0.3% by weight perfume oil and water ad 100%.

The invention relates also to an oral composition, comprising from 0.01 to 15% by weight, based on the total weight of the composition, of the compound of formula (1), and orally tolerable adjuvants.

Example of an oral composition:

10% by weight sorbitol

10% by weight glycerol

15% by weight ethanol

15% by weight propylene glycol 0.5% by weight sodium lauryl sulfate 0.25% by weight sodium methylcocyl taurate 0.25% by weight polyoxypropylene/polyoxyethylene block copolymer 0.10% by weight peppermint flavouring 0.1 to 0.5% by weight of a compound of formula (1) and 48.6% by weight water.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

The stilbene compounds of formula (1) used according to the invention are also suitable for the treatment of textile fibre materials. Such materials are undyed and dyed or printed fibre materials, e.g. of silk, wool, polyamide or polyurethanes, and especially cellulosic fibre materials of all kinds. Such fibre materials are, for example, natural cellulose fibres, such as cotton, linen, jute and hemp, as well as cellulose and regenerated cellulose. Preferred suitable textile fibre materials are made of cotton.

The stilbene compounds of formula (1) are also used in washing and cleaning formulations, e.g. in liquid and powder washing agents or softeners.

The stilbene compounds used according to the invention are also suitable for the treatment of plastics, especially for imparting antimicrobial properties to or preserving plastics, e.g. polyethylene, polypropylene, polyurethane, polyester, polyamide, polycarbonate, latex etc. Fields of use therefor are, for example, floor coverings, plastics coatings, plastics container and packaging materials; kitchen and bathroom utensils (e.g. brushes, shower curtains; sponges, bathmats), latex, filter materials (air and water filters), plastics articles used in the field of medicine, e.g. dressing materials, syringes, catheters etc., so-called "medical devices", gloves and mattresses.

Paper, for example papers used for hygiene purposes, may also be provided with anti-microbial properties using the stilbene compounds according to the invention.

It is also possible for nonwovens, e.g. nappies/diapers, sanitary towels, panty liners, and cloths for hygiene and household uses, to be provided with antimicrobial properties in accordance with the invention.

The stilbene compounds can be used especially also in household and all-purpose cleaners for cleaning and disinfecting hard surfaces.

A cleaning preparation has, for example, the following composition:

0.01 to 5% of the compound of formula (1)

3.0% octyl alcohol 4EO 1.3% fatty alcohol $C_8$–$C_{10}$ polyglucoside 3.0% isopropanol ad 100% water.

In addition to preserving cosmetic and household products, technical products, such as paper treatment liquors, printing thickeners of starch or of cellulose derivatives, surface-coatings and paints, can be preserved and provided with antimicrobial properties.

The stilbene compounds of formula (1) are also suitable for the antimicrobial treatment of wood and for the antimicrobial treatment of leather, the antimicrobial preservation of leather and the provision of leather with antimicrobial properties.

The compounds according to the invention are also suitable for the protection of cosmetic products and household products from microbial spoilage.

The following Examples serve to illustrate the invention but do not limit the invention to the Examples.

EXAMPLE 1

Preparation of 3,5-dihydroxystilbene

1st Step

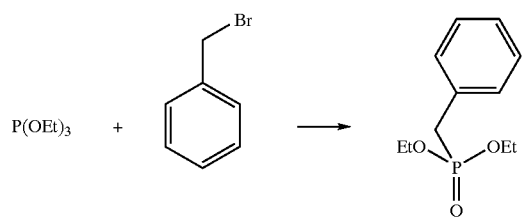

A mixture of 51.3 g (0.3 mol) of benzyl bromide and 79.1 g (0.5 mol) of triethyl phosphite is heated at 130° C. until the evolution of gas has ceased (3 h). The excess of triethyl phosphite is then removed under a water-jet vacuum. The crude product can be used for the next reaction without further purification.

Yield: 60 g (0.29 mol; 96.6% of theory)

2nd Step

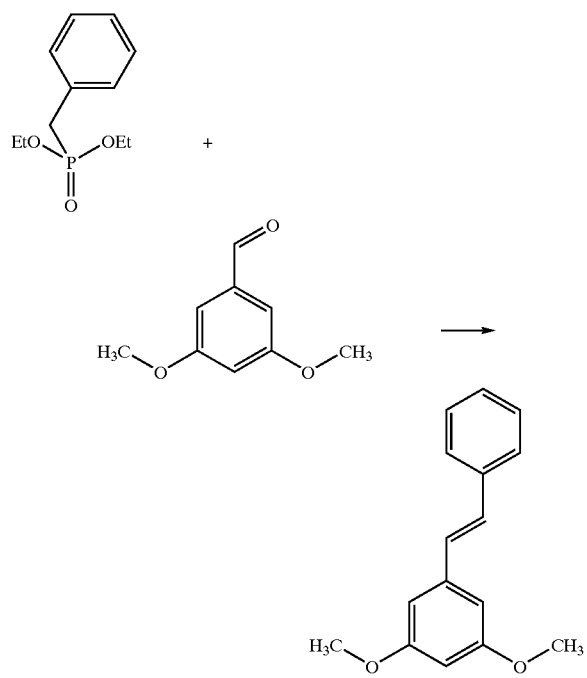

16.5 g (0.3 mol) of sodium methanolate are added at 0° C. to a solution of 60 g (0.29 mol) of crude diethylbenzyl phosphonate in 415 ml of anhydrous DMF. Then, at 0° C., a total of 50.0 g (0.3 mol) of 3,5-dimethoxybenzaldehyde is added in portions. After stirring for 1 hour at room temperature and heating for 1 hour under reflux, the product is precipitated by the addition of 660 ml of water/methanol (mixture ratio 2:1). Recrystallisation from water/methanol (2:1) yields 3,5-dimethoxystilbene in the form of colourless crystals.

Yield: 54.0 g (0.22 mol, 73.3% of theory)

3rd Step

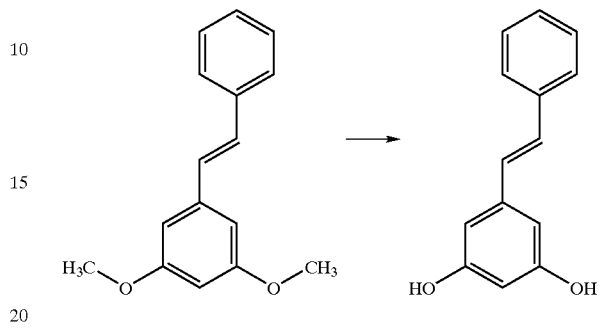

For demethylation, a homogeneous mixture of 54.0 g (0.22 mol) of 3,5-dimethoxystilbene and 40.0 g (0.35 mol) of pyridine hydrochloride is heated at about 165° C. for 3 hours. The cooled, oily reaction mass is then introduced into 1.2 liters of 2N hydrochloric acid and the crude product is isolated by extraction with diethyl ether. Recrystallisation from toluene yields 3,5-dlihydroxystilbene in the form of a pale-yellow powder.

Yield: 26.0 g (0.12 mol; 41.0% of theory)

EXAMPLE 2

Analogously to Example 1, reaction of 20.0 g (0.12 mol) of benzyl bromide, 38.9 g (0.23 mol) of triethyl phosphite and 15.9 g (0.12 mol) of 3-methoxybenzaldehyde yields 7.0 g of 3-hydroxystilbene, corresponding to formula (102)

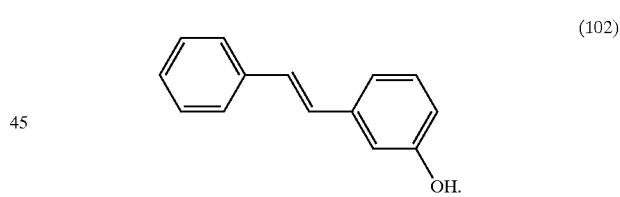

EXAMPLE 3

Determination of the Minimum Inhibiting Concentration (MIC) in the Agar Diffusion Test

| | |
|---|---|
| Medium: | Mueller-Hinton agar (Merck) |
| | * Sabouraud 4% glucose agar (Merck) |
| Dilution medium: | sterile 0.85% NaCl solution |
| Test organisms: | *Staphylococcus aureus* ATCC 9144 |
| | *Corynebacterium xerosis* ATCC 373 |
| | *Escherichia coli* NCTC 8196 |
| | *Pseudomonas aeruginosa* CIP A-22 |
| | *Candida albicans* ATCC 10231 |

-continued

| | |
|---|---|
| Incubation: | * Aspergillus niger ATCC 6275<br>24 hours at 37° C.<br>* 3 days at 28° C. |
| Test solution: | 5% stock solutions of all the test substances in a suitable solvent are prepared and diluted in serial dilutions to final concentrations of from 1000 ppm to 10 ppm. |
| Test principle: | 0.3 ml of the dilution stage in question is mixed with 15 ml of still-liquid nutrient medium. When the nutrient substrate has solidified 10 μl portions of the following organism dilution of the test strains in 0.85% NaCl solution are spotted onto the agar medium:<br>Staphylococcus aureus ATCC 9144  1:10 dilution<br>Corynebacterium xerosis ATCC 373  1:100 dilution<br>Escherichia coli NCTC 8196  1:100 dilution<br>Pseudomonas aeruginosa CIP A-22  1:100 dilution<br>Candida albicans ATCC 10231  1:10 dilution<br>* Aspergillus niger ATCC 6275  1:10 dilution<br>The plates are incubated at 37° C. for 24 hours (A. niger 3 days at 28° C.) and then the highest dilution of the test substance at which growth is just no longer discernible (corresponds to MIC) is determined. |

The results show that the test substances exhibit strong antimicrobial activity against gram-postive and gram-negative bacteria and also fungi.

The test results for the compounds listed below are given in Table 1:

General Formula

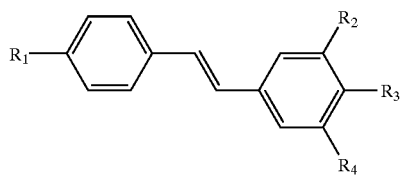

| Compound of formula | $R_1$ | $R_2$ | $R_3$ | $R_4$ |
|---|---|---|---|---|
| (101) | H | OH | H | OH |
| (102) | H | OH | H | H |
| (103) | OH | OH | H | OH |
| (104) | H | H | $N(CH_3)_2$ | H |
| (105) | OH | H | H | H |
| (106) | OH | H | Cl | H |

EXAMPLES 4 to 87

Solid-phase Synthesis Method

The following hydroxystilbenes are synthesised in accordance with known procedures (R. Willard et al., Chemistry & Biology, 2, 1995, 45–51).

The reaction is carried out in accordance with the following scheme:

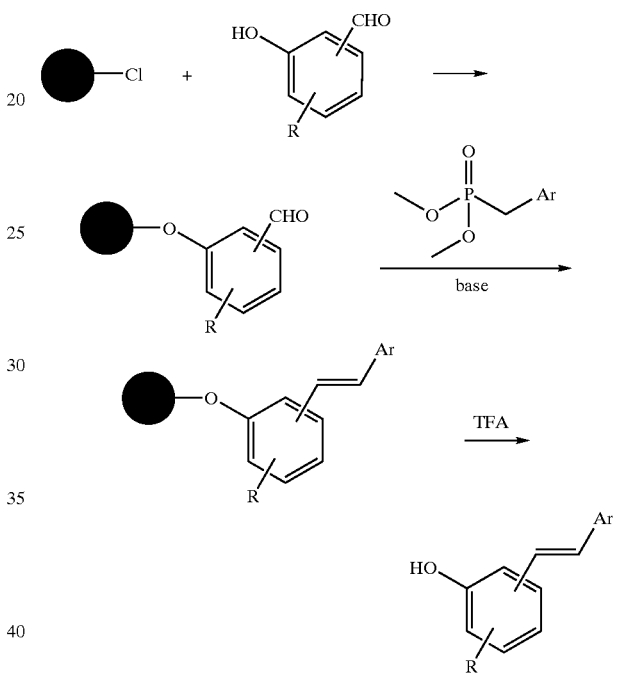

Using this method a matrix of 12×7=84 hydroxystilbenes having the following structural scope is synthesised:

TABLE 1

| Organisms | Compound of formula (101)[1] | Compound of formula (102)[2] | Compound of formula (103)[3] | Compound of formula (104)[4] | Compound of formula (105)[5] | Compound of formula (106)[6] |
|---|---|---|---|---|---|---|
| S. aureus | 100 | 100 | 600 | 300 | — | 10 |
| C. xerosis | — | — | 100 | — | — | — |
| E. coli | 100 | 100 | 600 | — | — | — |
| P. aeruginosa | 100 | — | 600 | — | — | — |
| C. albicans | 100 | 100 | 600 | 600 | — | — |
| A. niger | 100 | 10 | — | — | 10 | 600 |

(all values MIC concentrations in ppm)
— = not tested
[1] solution EtOH
[2] solution in DMSO
[3] solution in EtOH
[4] solution in DMSO
[5] solution in DMSO
[6] solution in DMSO General Formula

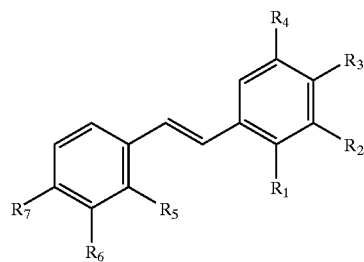

| Comp. of formula | R₁ | R₂ | R₃ | R₄ | R₅ | R₆ | R₇ |
|---|---|---|---|---|---|---|---|
| 107 | H | H | OH | H | H | H | H |
| 108 | H | OH | H | H | H | H | H |
| 109 | H | OH | OMe | H | H | H | H |
| 110 | H | OEt | OH | H | H | H | H |
| 111 | H | OMe | OH | H | H | H | H |
| 112 | OH | H | OMe | H | H | H | H |
| 113 | OH | H | H | H | H | H | H |
| 114 | H | OH | OMe | OMe | H | H | H |
| 115 | H | Me | OH | Me | H | H | H |
| 116 | OH | Me | H | H | H | H | H |
| 117 | OH | H | OBzl | H | H | H | H |
| 118 | OMe | H | OH | H | H | H | H |
| 119 | H | H | OH | H | H | H | Cl |
| 120 | H | OH | H | H | H | H | Cl |
| 121 | H | OH | OMe | H | H | H | Cl |
| 122 | H | OEt | OH | H | H | H | Cl |
| 123 | H | OMe | OH | H | H | H | Cl |
| 124 | OH | H | OMe | H | H | H | Cl |
| 125 | OH | H | H | H | H | H | Cl |
| 126 | H | OH | OMe | OMe | H | H | Cl |
| 127 | H | Me | OH | Me | H | H | Cl |
| 128 | OH | Me | H | H | H | H | Cl |
| 129 | OH | H | OBzl | H | H | H | Cl |
| 130 | OMe | H | OH | H | H | H | Cl |
| 131 | H | H | OH | H | H | H | OMe |
| 132 | H | OH | H | H | H | H | OMe |
| 133 | H | OH | OMe | H | H | H | OMe |
| 134 | H | OEt | OH | H | H | H | OMe |
| 135 | H | OMe | OH | H | H | H | OMe |
| 136 | OH | H | OMe | H | H | H | OMe |
| 137 | OH | H | H | H | H | H | OMe |
| 138 | H | OH | OMe | OMe | H | H | OMe |
| 139 | H | Me | OH | Me | H | H | OMe |
| 140 | OH | Me | H | H | H | H | OMe |
| 141 | OH | H | OBzl | H | H | H | OMe |
| 142 | OMe | H | OH | H | H | H | OMe |
| 143 | H | H | OH | H | H | H | Ph |
| 145 | H | OH | H | H | H | H | Ph |
| 146 | H | OH | OMe | H | H | H | Ph |
| 147 | H | OEt | OH | H | H | H | Ph |
| 148 | H | OMe | OH | H | H | H | Ph |
| 149 | OH | H | OMe | H | H | H | Ph |
| 150 | OH | H | H | H | H | H | Ph |
| 151 | H | OH | OMe | OMe | H | H | Ph |
| 152 | H | Me | OH | Me | H | H | Ph |
| 153 | OH | Me | H | H | H | H | Ph |
| 154 | OH | H | OBzl | H | H | H | Ph |
| 155 | OMe | H | OH | H | H | H | Ph |
| 156 | H | H | OH | H | ⌬ | | H |
| 157 | H | OH | H | H | ⌬ | | H |

-continued

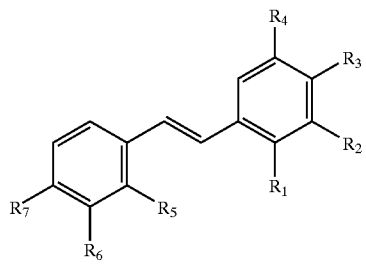

| Comp. of formula | R₁ | R₂ | R₃ | R₄ | R₅ | R₆ | R₇ |
|---|---|---|---|---|---|---|---|
| 158 | H | OH | OMe | H | ⌬ | | H |
| 159 | H | OEt | OH | H | ⌬ | | H |
| 160 | H | OMe | OH | H | ⌬ | | H |
| 161 | OH | H | OMe | H | ⌬ | | H |
| 162 | OH | H | H | H | ⌬ | | H |
| 163 | H | OH | OMe | OMe | ⌬ | | H |
| 164 | H | Me | OH | Me | ⌬ | | H |
| 165 | OH | Me | H | H | ⌬ | | H |
| 166 | OH | H | OBzl | H | ⌬ | | H |
| 167 | OMe | H | OH | H | ⌬ | | H |
| 168 | H | H | OH | H | Me | H | H |
| 169 | H | OH | H | H | Me | H | H |
| 170 | H | OH | OMe | H | Me | H | H |
| 171 | H | OEt | OH | H | Me | H | H |
| 172 | H | OMe | OH | H | Me | H | H |
| 173 | OH | H | OMe | H | Me | H | H |

-continued

| Comp. of formula | R₁ | R₂ | R₃ | R₄ | R₅ | R₆ | R₇ |
|---|---|---|---|---|---|---|---|
| 174 | OH | H | H | H | Me | H | H |
| 175 | H | OH | OMe | OMe | Me | H | H |
| 176 | H | Me | OH | Me | Me | H | H |
| 177 | OH | Me | H | H | Me | H | H |
| 178 | OH | H | OBzl | H | Me | H | H |
| 179 | OMe | H | OH | H | Me | H | H |
| 180 | H | H | OH | H | H | H | Me |
| 181 | H | OH | H | H | H | H | Me |
| 182 | H | OH | OMe | H | H | H | Me |
| 183 | H | OEt | OH | H | H | H | Me |
| 184 | H | OMe | OH | H | H | H | Me |
| 185 | OH | H | OMe | H | H | H | Me |
| 186 | OH | H | H | H | H | H | Me |
| 187 | H | OH | OMe | OMe | H | H | Me |
| 188 | H | Me | OH | Me | H | H | Me |
| 189 | OH | Me | H | H | H | H | Me |
| 190 | OH | H | OBzl | H | H | H | Me |
| 191 | OMe | H | OH | H | H | H | Me |

Me = methyl
Et = ethyl
Bzl = benzyl

The microbiological data obtained are summarised in Table 2.

TABLE 2

MIC values in ppm for various microorganisms*)

| Comp. of formula | S. heminis | E. coli | P. aeruginosa | C. albicans | A. niger |
|---|---|---|---|---|---|
| 107 | 100 | >100 | >100 | >100 | 100 |
| 105 | 60 | 30 | 100 | 30 | 30 |
| 109 | >100 | >100 | >100 | >100 | 100 |
| 110 | >100 | >100 | >100 | >100 | >100 |
| 111 | >100 | >100 | >100 | >100 | 100 |
| 112 | — | — | — | — | — |
| 113 | 100 | 100 | >100 | 60 | 60 |
| 114 | >100 | 100 | >100 | >100 | 100 |
| 115 | — | — | — | — | — |
| 116 | 60 | 60 | 100 | 60 | 60 |
| 117 | >100 | >100 | >100 | >100 | 100 |
| 118 | — | — | — | — | — |
| 119 | 7.5 | >100 | >100 | 15 | 100 |
| 120 | 7.5 | 7.5 | >100 | 7.5 | 30 |
| 121 | >100 | >100 | >100 | >100 | >100 |
| 122 | >100 | >100 | >100 | >100 | >100 |
| 123 | >100 | >100 | >100 | >100 | 100 |
| 124 | 15 | 15 | >100 | 30 | 30 |
| 125 | 60 | 15 | 100 | 60 | 60 |
| 126 | >100 | >100 | >100 | 100 | 100 |
| 127 | — | — | — | — | — |
| 128 | >100 | >100 | >100 | >100 | 100 |
| 129 | — | — | — | — | — |
| 130 | — | — | — | — | — |
| 131 | >100 | >100 | >100 | >100 | >100 |
| 132 | >100 | >100 | >100 | >100 | >100 |

TABLE 2-continued

MIC values in ppm for various microorganisms*)

| Comp. of formula | S. heminis | E. coli | P. aeruginosa | C. albicans | A. niger |
|---|---|---|---|---|---|
| 133 | >100 | >100 | >100 | >100 | >100 |
| 134 | >100 | >100 | >100 | >100 | >100 |
| 135 | >100 | >100 | >100 | >100 | >100 |
| 136 | — | — | — | — | — |
| 137 | >100 | 100 | >100 | >100 | >100 |
| 138 | >100 | >100 | >100 | >100 | >100 |
| 139 | — | — | — | — | — |
| 140 | >100 | >100 | >100 | >100 | 100 |
| 141 | — | — | — | — | — |
| 142 | — | — | — | — | — |
| 143 | >100 | >100 | >100 | >100 | >100 |
| 145 | >100 | >100 | >100 | >100 | >100 |
| 146 | >100 | >100 | >100 | >100 | >100 |
| 147 | >100 | >100 | >100 | >100 | >100 |
| 148 | >100 | >100 | >100 | >100 | >100 |
| 149 | — | — | — | — | — |
| 150 | >100 | >100 | >100 | >100 | >100 |
| 151 | >100 | >100 | >100 | >100 | >100 |
| 152 | — | — | — | — | — |
| 153 | >100 | >100 | >100 | >100 | >100 |
| 154 | — | — | — | — | — |
| 155 | — | — | — | — | — |
| 156 | 7.5 | 60 | >100 | 15 | 30 |
| 157 | 7.5 | 15 | >100 | 15 | 60 |
| 158 | >100 | >100 | >100 | >100 | >100 |
| 159 | >100 | >100 | >100 | >100 | 100 |
| 160 | >100 | >100 | >100 | >100 | 100 |
| 161 | — | — | — | — | — |
| 162 | 7.5 | 30 | >100 | 30 | 15 |
| 163 | >100 | >100 | >100 | >100 | 100 |
| 164 | — | — | — | — | — |
| 165 | 100 | >100 | >100 | >100 | 100 |
| 166 | — | — | — | — | — |
| 167 | — | — | — | — | — |
| 168 | 7.5 | 30 | 100 | 15 | 30 |
| 169 | 30 | 60 | 100 | 30 | 30 |
| 170 | >100 | >100 | >100 | >100 | >100 |
| 171 | >100 | >100 | >100 | >100 | >100 |
| 172 | >100 | >100 | >100 | 10 | >100 |
| 173 | — | — | — | — | — |
| 174 | 60 | 100 | >100 | 60 | 60 |
| 175 | 60 | 60 | 100 | 60 | 100 |
| 176 | — | — | — | — | — |
| 177 | 30 | 60 | >100 | 60 | 60 |
| 178 | — | — | — | — | — |
| 179 | — | — | — | — | — |
| 180 | 100 | >100 | >100 | >100 | >100 |
| 181 | 15 | 15 | 100 | 15 | 30 |
| 182 | >100 | >100 | >100 | >100 | >100 |
| 183 | >100 | >100 | >100 | >100 | >100 |
| 184 | >100 | >100 | >100 | >100 | 100 |
| 185 | — | — | — | — | — |
| 186 | 30 | 30 | 100 | 30 | 60 |
| 187 | >100 | >100 | >100 | >100 | >100 |
| 188 | — | — | — | — | — |
| 189 | >100 | 100 | >100 | >100 | >100 |
| 190 | — | — | — | — | — |
| 191 | — | — | — | — | — |

— = not determined
*)The MIC values were obtained by measuring the optical density at substance concentrations between 100; 10 and 1 ppm. In that respect some of the data are indicative values for the activity. The MIC values of the compounds having good activity were obtained by measuring the optical density at concentrations between 120; 60; 30; 15; 7.5; 3.75 ppm.

Determination of the Minimum Inhibiting Concentration (MIC Value) in Microtitre Plates Nutrient Medium Casein/soybean flour peptone bouillon for the preparation of the precultures of the test bacteria and yeast.

Mycological slant agar for the preculture of moulds.

Examples of Test Organisms

| | |
|---|---|
| Bacteria: | *Staphylococcus hominis* DSM 20328 |
| | *Escherichia coli* NCTC 8196 |
| | *Pseudomonas aeruginosa* CIP A-22 |
| Yeast: | *Candida albicans* ATCC 10231 |
| Mould: | *Aspergillus niger* ATCC 6275 |

Procedure

The test substances are predissolved in dimethyl sulfoxide (DMSO) and tested in a serial dilution of 1:2.

Bacteria and yeast are cultured overnight in CASO bouillon, the mould on mycological slant agar and rinsed off with 10 ml of 0.85% sodium chloride solution (+0.1% TritonX-100).

All test organisms are adjusted to an organism count of $1.5\times10^6$ CFU/ml with 0.85% sodium chloride solution.

The test substances are prepipetted into microtitre plates in an amount of 8 µl per well.

Previously diluted organism substances are diluted 1:100 in CASO bouillon (bacteria and yeast) and Sabouraud 2% glucose bouillon (mould) and added to the test substances in an amount of 192 µl per well.

The test batches are incubated for 48 hours at 37° C. (bacteria and yeast) or for 5 days at 28° C. (mould).

After incubation, the growth is determined by reference to the turbidity of the test batches (optical density) at 620 nm in a microplate reader.

The minimum inhibiting concentration (MIC value) is the concentration of substance at which (compared with the growth control) an appreciable inhibition of the growth ($\leq$20% growth) of the test organisms is ascertained.

One microtiter plate is used for each test organism and substance concentration. All substances tested in duplicate.

What is claimed is:

1. A compound of formula

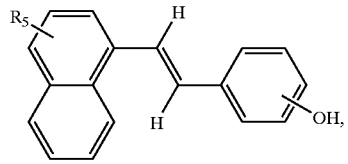

(3)

wherein

R$_5$ is hydrogen, halogen, hydroxy, $C_1$–$C_{16}$alkyl, $C_1$–$C_{16}$alkoxy, phenyl; $C_1$–$C_3$phenylalkyl; $C_6$–$C_{10}$aryloxy; amino; mono-$C_1$–$C_5$alkylamino; di-$C_1$–$C_5$alkylamino; or —NO$_2$.

2. A compound according to claim 1, wherein

R$_5$ is hydrogen.

3. A method of antimicrobial treatment, deodorisation and disinfection of the skin, mucosa and hair, which comprises applying thereto an antimicrobially effective amount of a hydroxystilbene compound of formula

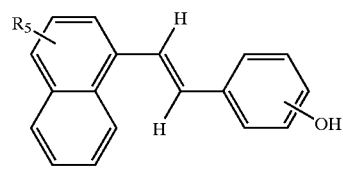

(3)

wherein R$_5$ is hydrogen, halogen, hydroxy, $C_1$–$C_{16}$alkoxy, $C_1$–$C_{16}$alkoxy, phenyl; $C_1$–$C_3$phenylalkyl; $C_6$–$C_{10}$aryloxy, amino, mono-$C_1$–$C_5$alkylamino, di-$C_1$–$C_5$alkylamino, or —NO$_2$.

4. A process for the preparation of compounds of formula

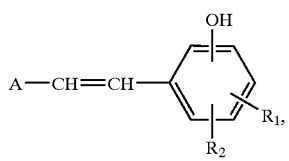

(1)

wherein

A is a radical of formula

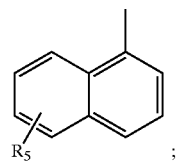

(1a)

or a radical of formula

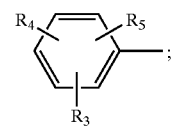

(1b)

and

R$_1$, R$_2$, R$_3$, R$_4$ and R$_5$ are each independently of the others hydrogen, halogen, hydroxy, $C_1$–$C_{16}$alkyl, $C_1$–$C_{16}$alkoxyl, phenyl; $C_1$–$C_3$phenylalkyl; $C_6$–$C_{10}$aryloxy, amino, mono-$C_1$–$C_5$alkylamino, di-$C_1$–$C_5$alkyamino, or —NO$_2$, which process comprises preparing them in a solid-phases synthesis using a trityl resin in accordance with the following scheme:

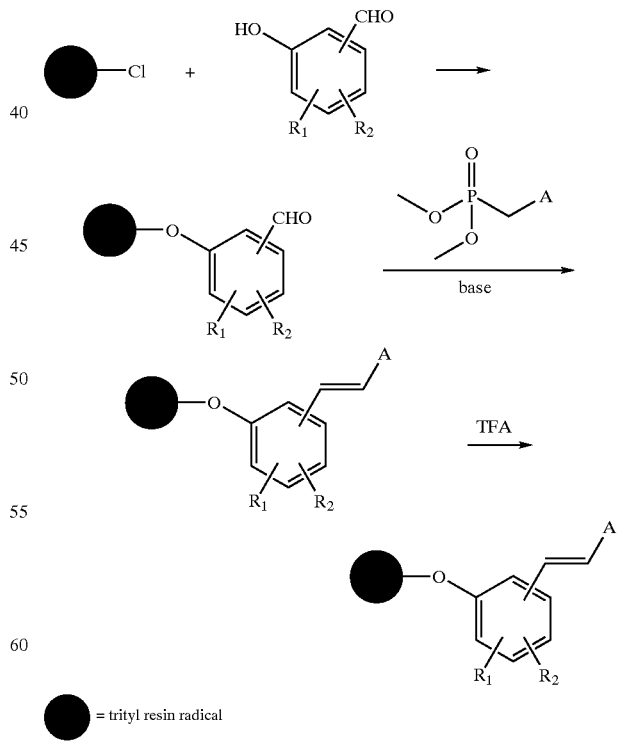

● = trityl resin radical

* * * * *